United States Patent [19]

Bohn et al.

[11] Patent Number: 4,592,863

[45] Date of Patent: Jun. 3, 1986

[54] PROTEIN PP$_{20}$, A PROCESS FOR OBTAINING IT, AND ITS USE

[75] Inventors: Hans Bohn, Marburg; Wilhelm Winckler, Wenkbach, both of Fed. Rep. of Germany

[73] Assignee: Behringwerke Aktiengesellschaft, Fed. Rep. of Germany

[21] Appl. No.: 662,895

[22] Filed: Oct. 19, 1984

[30] Foreign Application Priority Data

Oct. 22, 1983 [DE] Fed. Rep. of Germany ....... 3338480

[51] Int. Cl.$^4$ ..................... C07K 15/00; A61K 35/50; A61K 39/395; C07G 7/26
[52] U.S. Cl. ..................................... 530/350; 424/85; 424/88; 436/543; 436/547; 530/414; 530/415; 530/416; 530/418; 530/420; 530/806
[58] Field of Search ....................... 260/112 R, 112 B; 424/85, 88; 436/543, 547

[56] References Cited

U.S. PATENT DOCUMENTS

| | | | |
|---|---|---|---|
| 4,301,064 | 11/1981 | Bohn | 260/112 R |
| 4,348,316 | 9/1982 | Bohn | 260/112 R |
| 4,402,872 | 9/1983 | Bohn | 260/112 R |
| 4,468,345 | 8/1984 | Bohn et al. | 260/112 R |
| 4,500,451 | 2/1985 | Bohn et al. | 260/112 R |

OTHER PUBLICATIONS

"New Soluble Placental Tissue Proteins", Hans Bohn, Research Laboratories of Behringwerke AG, Marburg-/Lahn, La Ricerca Clin. Lab. 12, 221, 1982, pp. 221-230.

*Primary Examiner*—Howard E. Schain
*Attorney, Agent, or Firm*—Finnegan, Henderson, Farabow, Garrett & Dunner

[57] ABSTRACT

The protein PP$_{20}$ is described, this having the following characteristics:

(a) an electrophoretic mobility which is somewhat larger than that of albumin,
(b) an isoelectric point of 4.65±0.1,
(c) a sedimentation coefficient s$_{20,w}$ of 4.1±0.1 S,
(d) a molecular weight determined by electrophoresis in sodium dodecyl sulfate (SDS)-containing polyacrylamide gel of 50,000±10,000, the molecules of PP$_{20}$ being composed of apparently identical subunits which have a molecular weight of 27,000±3,000 and are held together non-covalently,
(e) an extinction coefficient E$_{1cm}$$^{1\%}$ (280 nm) of 9.5±0.6,
(f) a carbohydrate content of 3.0±1.3%, including mannose 0.14±0.05%, fucose 0.13±0.05%, galactose 0.61±0.2%, glucose 0.39±0.2%, N-acetylglucosamine 0.95±0.3%, N-acetylgalactosamine 0.18±0.1%, and N-acetylneuraminic acid 0.6±0.4%.
(g) a specified aminoacid composition, and a process for obtaining it is described.

This protein can be used to obtain antisera and to design immunochemical methods which can be used to detect and determine this protein, in order to monitor pregnancy or to detect or check the course of diseases.

3 Claims, 2 Drawing Figures

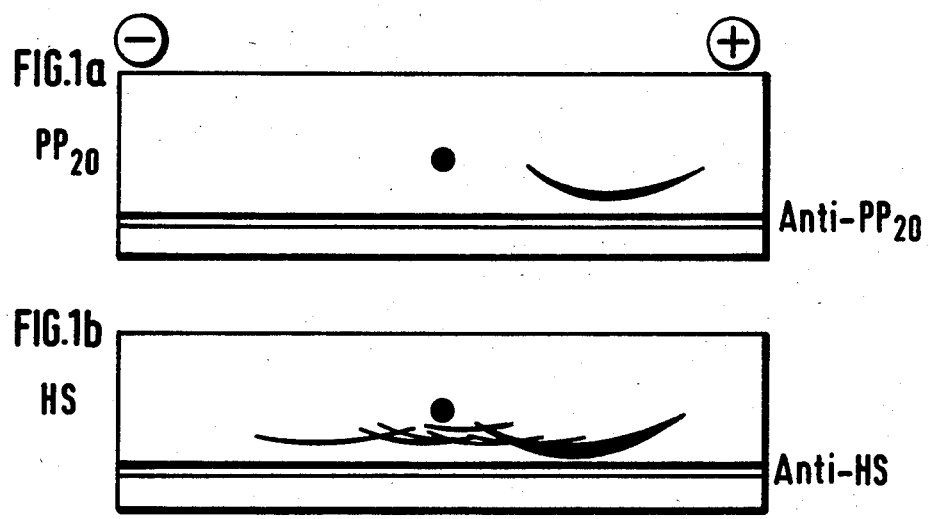

PROTEIN PP₂₀, A PROCESS FOR OBTAINING IT, AND ITS USE

The invention relates to a new protein $PP_{20}$, to a process for enriching it and obtaining it from an extract of human placentae, and to its use.

Many soluble proteins originating from human placentae have already been detected in extracts of this tissue (Bohn, H., La Ricerca Clin. Lab. 12, 221, 1982). The present patent application describes the isolation and characterization of a new soluble protein, called $PP_{20}$.

The invention relates to the protein $PP_{20}$, which has the following characteristics:

(a) an electrophoretic mobility which is somewhat larger than that of albumin,
(b) an isoelectric point of $4.65 \pm 0.1$,
(c) a sedimentation coefficient $s_{20,w}$ of $4.1 \pm 0.1$ S,
(d) a molecular weight determined by electrophoresis in sodium dodecyl sulfate (SDS)-containing polyacrylamide gel of $50,000 \pm 10,000$, the molecules of $PP_{20}$ being composed of apparently identical subunits which have a molecular weight of $27,000 \pm 3,000$ and are held together non-covalently,
(e) an extinction coefficient $E_{1\ cm}^{1\%}$ (280 nm) of $9.5 + 0.6$,
(f) a carbohydrate content of $3.0 \pm 1.3\%$, including mannose $0.14 \pm 0.05\%$, fucose $0.13 \pm 0.05\%$, galactose $0.61 \pm 0.02\%$, glucose $0.39 \pm 0.2\%$, N-acetylglucosamine $0.95 \pm 0.3\%$, N-acetylgalactosamine $0.18 \pm 0.1\%$, N-acetylneuraminic acid $0.6 \pm 0.4\%$, and
(g) the following aminoacid composition:

| Aminoacid | (Residues per 100 residues) mole-% | Coefficient of variation |
|---|---|---|
| Lysine | 5.36 | 0.26 |
| Histidine | 3.10 | 7.30 |
| Arginine | 3.39 | 0.63 |
| Aspartic acid | 11.45 | 1.05 |
| Threonine | 8.63 | 1.31 |
| Serine | 3.70 | 1.34 |
| Glutamic acid | 9.65 | 1.61 |
| Proline | 5.64 | 6.40 |
| Glycine | 6.96 | 1.12 |
| Alanine | 4.76 | 1.49 |
| Cystine ½ | 2.86 | 2.47 |
| Valine | 6.22 | 0.23 |
| Methionine | 1.87 | 1.51 |
| Isoleucine | 5.76 | 3.44 |
| Leucine | 11.76 | 2.65 |
| Tyrosine | 2.55 | 3.33 |
| Phenylalanine | 4.12 | 1.55 |
| Tryptophan | 2.17 | 1.30 |

The following may be mentioned to explain the characterizing features of the tissue protein:

The electrophoretic mobility was determined on cellulose acetate films (supplied by Sartorius) using sodium diethylbarbiturate buffer, pH 8.6, in a Beckman Instruments Microzone R 200 apparatus.

The isoelectric point was determined using a column (440 ml) supplied by LKB, Stockholm. The so-called Ampholin ® mixture for the investigation of the glycoprotein had a pH range from 4.0 to 6.0.

The sedimentation coefficient was determined in double-sector cells using the UV scanner technique at 280 nm in an analytical ultracentrifuge supplied by Beckman (Spinco apparatus, model E) at 60,000 rpm. The solvent used was a 0.05M phosphate buffer (pH 6.8) which contained 0.2 mole/liter NaCl. The protein concentration was adjusted to an optical density of about 3. The sedimentation coefficient was converted to the basis of water at 20° C.

For the electrophoretic determination of the molecular weight in SDS-PAA gel, the gel used contained 7.5 g/100 ml polyacrylamide (PPA) and 0.1 g/100 ml sodium dodecyl sulfate (SDS).

To investigate for subunits, before application the protein was heated at 60° C. for 10 minutes in a solution which contained 1 g/100 ml SDS and, where appropriate, 1 g/100 ml mercaptoethanol. The comparison substances used were human placental lactogen (HPL) and human albumin and its aggregates.

To determine the extinction coefficient, a 0.10% strength (g/100 ml) solution of the substance in distilled water was prepared.

The analysis of the carbohydrates was carried out as follows: After hydrolysis of the glycosidic bonds, the liberated neutral sugars were separated as their borate complexes on an anion exchanger column (Y. C. Lee et al., Anal. Biochem. 27, 567, 1969), subjected to a color reaction in the eluate by admixture of Cu(I) bicinchoninate reagent (K. Mopper and M. Gindler, Anal. Biochem. 56, 440, 1973) and determined quantitatively using rhamnose as the internal standard. The aminosugars were detected and determined by their reaction with ninhydrin. The neuraminic acid content was determined by the method of Warren (Methods in Enzymology, Vol. VI, 463–465, 1963).

The aminoacid analysis was carried out by the method of S. Moore, D. H. Spackman, W. H. Stein, Anal. Chem. 30. 1185, 1958, using a Multichrom B liquid chromatograph supplied by Beckman. ½-Cystine was determined as cysteic acid after oxidation of the protein with performic acid (S. Moore et al., Anal. Chem. 30, 1185, 1958) followed by chromatography (S. Moore, J. Biol. Chem., 238, 235, 1963). The tryptophan content was determined by direct photometric determination by the method of H. Edelhoch, Biochemistry 6, 1948, 1967.

$PP_{20}$ has the following properties which can be used in a process for its isolation, the measures chosen being apppropriate for these properties:

(1) It is precipitated from aqueous solutions with ammonium sulfate at pH 7 and 30–70% saturation;

(2) It is precipitated with water-soluble acridine bases, for example 2-epoxy-6,9-diaminoacridine lactate, at pH values between 4 and 7 and at a concentration of the base of 0.2 to 0.4 g/100 ml;

(3) On electrophoresis at pH 8.6, it migrates somewhat faster than does albumin;

(4) On isoelectric focusing, it appears in the pH range from 4.55 to 4.75, with a maximum at 4.65;

(5) On gel filtration with Sephadex ® or acrylamide agarose, it behaves like proteins having molecular weights from 30,000 to 70,000;

(6) In contrast to most other proteins, it is not adsorbed onto bentonite (calcium bentonite) in dilute salt solutions having a conductivity of about 0–2 mS;

(7) It can be bound to weakly basic ion exchangers, such as, for example, DEAE-cellulose or DEAE-sephadex, at a conductivity of about 0–2 mS and a pH of about 7 to 9, and can be eluted with concentrated salt solutions, for example solutions containing 1–5 g NaCl in 100 ml;

(8) It can be enriched and isolated from an aqueous solution by immunoadsorption.

Thus the invention also relates to a process for obtaining $PP_{20}$, which comprises fractionating an extract from human placentae using the abovementioned properties.

Accordingly, the invention relates to a process for obtaining or enriching $PP_{20}$, which comprises subjecting an extract obtained from placentae using a dilute salt or buffer solution to one or more of the following measures:

(a) precipitation of the protein $PP_{20}$ with ammonium sulfate in the pH range from 5 to 8 and at 30–70% saturation;

(b) precipitation of the protein $PP_{20}$ with a water-soluble acridine base at a pH between 4 and 7 and a concentration of the base of 0.2–0.4 g/100 ml;

(c) preparative zone electrophoresis, the protein fraction which migrates somewhat faster than albumin being isolated;

(d) gel filtration or ultrafiltration, proteins in the molecular weight range from 30,000 to 70,000 being isolated;

(e) isoelectric focusing, proteins in the pH range from 4.55 to 4.75 being isolated;

(f) adsorption of accompanying proteins onto bentonite (bentonite A, calcium bentonite, Erbslöh & Co., Geisenheim a. Rhein), $PP_{20}$ remaining in solution;

(g) adsorption of the protein $PP_{20}$ onto a weakly basic ion exchanger and elution of this protein;

(h) enrichment by immunoadsorption.

Of course, apart from ammonium sulfate, it is also possible to use for the precipitation of $PP_{20}$ other neutral salts customarily employed in preparative biochemistry. Apart from an acridine base, it is also possible to use a water-soluble derivative of a quinoline base, as are known for protein fractionation, within the scope of the process according to the invention. For the isolation of the protein it is also possible to use other measures which are appropriate for its electrophoretic behavior, its isoelectric point and its molecular weight and which are suitable for separating a protein having the properties indicated from other proteins. It is possible to use for this purpose the various methods of preparative electrophoresis, isoelectric focusing, gel filtration, gel chromatography or ultrafiltration or even the property of $PP_{20}$ of being able to be bound to weakly basic ion exchangers and eluted again therefrom.

The $PP_{20}$ can be isolated by an appropriate combination of the measures mentioned which bring about enrichment of $PP_{20}$ or separation of this protein from other proteins.

Accordingly, the present invention is regarded as relating to the individual steps for enrichment of $PP_{20}$ and to the process for the purification of $PP_{20}$ which results from combination of the measures for enrichment.

The steps for the enrichment and isolation of $PP_{20}$ indicated in the example are by no means all obligatory, nor need they be carried out in the sequence described in the example.

It would be possible to use the extract from human placentae directly for immunoadsorption. However, since the concentration of $PP_{20}$ in placental extract is relatively low, it is appropriate first specifically to enrich the protein $PP_{20}$ by an initial fractionation of the extract using methods which are suitable for the fractionation of proteins on a relatively large scale; for example by fractional precipitation with neutral salts or organic cations, by gel filtration or by ion exchange chromatography. It is also possible to replace the immunoadsorption step by using other methods of separation, for example by preparative electrophoresis or isoelectric focusing.

Gel filtration on acrylamide agarose AcA 34 and reverse immunoadsorption have proved to be utilizable for the final purification of $PP_{20}$ in the last stage of isolation.

On average, 0.5 mg of this protein can be extracted with physiological saline solution from a mature human placenta (600 g). Apart from the placenta, $PP_{20}$ has been detected in humans only in spleen extracts.

Other human organs (for example heart, lung, skin, stomach, kidney, uterus, liver, adrenals, colon and bladder) either do not contain this protein or contain it only in considerably lower concentration. Moreover, in serum and in other human body fluids, $PP_{20}$ normally does not occur or occurs only in traces (less than 1 mg/l).

Apart from the parameters indicated, it is also possible to use for the detection and determination of $PP_{20}$, for example in a fraction from a separation operation, immunochemical methods, since $PP_{20}$ has antigenic properties. Specific antibodies are formed on immunization of animals with this protein.

An antiserum which can be utilized for this purpose can be obtained as follows: On fractionation of the placental extract using an acridine base and ammonium sulfate by the method of Bohn (Arch. Gynäk. 210 (1971), 440–457), $PP_{20}$ is found mainly in placental fraction II. When this fraction is further fractionated by gel filtration through Sephadex G-150, $PP_{20}$ appears in the range of low molecular weight proteins (range: 30,000–70,000). When, after dialysis against a 0.01 molar tris HCl buffer (pH 7.0), an adequate amount of bentonite A is added to this fraction, then most proteins are absorbed onto the bentonite, while $PP_{20}$ remains dissolved in the supernatant. Immunization of rabbits with this supernatant results in a polyvalent antiserum which principally contains antibodies against $PP_{20}$. This antiserum can be made essentially specific against the antigen $PP_{20}$ by absorption with normal human serum and with certain placental proteins, such as alpha 1-fetoprotein (AFP) and ferritin ($PP_2$).

An antiserum of this type can be used on the one hand for immunological detection of $PP_{20}$, and on the other hand for the preparation of an immunoadsorbent which can be employed for enrichment and isolation of $PP_{20}$.

Monospecific antisera can be prepared by immunization of animals by known methods using the highly purified $PP_{20}$ obtained in accordance with the present application.

FIG. 1a shows the immunological reaction of $PP_{20}$ with a specific antiserum from a rabbit after separation in an electrical field in agar-containing gel.

For comparison with this, FIG. 1b shows the separation of the proteins in the serum, visualized by their immune reaction with an antiserum against human serum (HS) from a rabbit.

It is also possible to use for the immunological detection of $PP_{20}$ the Ouchterlony gel diffusion technique (cf. Schultze and Heremans, Molecular Biology of Human Proteins, Vol. 1, pg. 134) or, if necessary, more sensitive methods, such as radioimmunoassays or enzyme immunoassays.

The detection and determination of $PP_{20}$ have diagnostic importance: $PP_{20}$ is a protein which, apart from in the placenta, appears to occur in relatively high concentration only in the spleen. During pregnancy as well as organic diseases, for example tumors, the concentration of this tissue protein in the serum or in other body fluids of the patients may increase above normal. Thus, $PP_{20}$ can be employed as a marker to monitor pregnancy or to detect and check the course of diseases.

Thus, $PP_{20}$ can be used for the preparation of specific antibodies against this protein and for the design of immunochemical methods (for example radioimmunoassay, enzyme immunoassay) for the detection and determination of this protein.

The invention is illustrated by the example below.

EXAMPLE (A) Extraction of the placentae and fractionation of the extract using an acridine base and ammonium sulfate 1,000 kg of deep-frozen human placentae were comminuted in a cutter-mixer and extracted with 1,000 liters of a 0.4% strength (g/100 ml) saline solution. After removal of the residual tissue by centrifugation, the extract was adjusted to pH 6.0 with 20% strength (g/100 ml) acetic acid, and 200 liters of a 3% strength (g/100 ml) solution of 2-ethoxy-6,9-diaminoacridine lactate (Rivanol®, Hoechst AG) were added, with stirring. The precipitate was removed by centrifugation, and 500 liters of a 2.5% strength (g/100 ml) NaCl solution were added and the mixture was stirred for 4 hours. The precipitated chloride of 2-ethoxy-6,9-diaminoacridine was removed by centrifugation. Part of the accompanying proteins were precipitated out of the supernatant by addition of 25% (g/100 ml) ammonium sulfate. Most of the protein $PP_{20}$ remained in solution. It was precipitated from this by addition of further ammonium sulfate (20 g/100 ml) and then removed by centrifugation. This resulted in about 3 kg of a moist paste which is called fraction A below.

(B) Gel filtration on Sephadex G-150

500 g of fraction A were dissolved in water, about 2.5 g of bentonite A (supplied by Erbslöh & Co., Geisenheim/Rh.) were added to remove Rivanol® still present and, after centrifugation, the solution was dialyzed against 0.01 mole/liter tris HCl buffer (pH 8.0) which contained 0.05% (g/100 ml) $NaN_3$ (buffer solution I). The remaining solution was applied to a column (20×100 cm) packed with Sephadex G-150 and eluted with buffer solution I. The eluates containing the low molecular weight proteins (MW 30,000 to 70,000) were combined and 45 g/100 ml of ammonium sulfate were added to precipitate the proteins. The precipitate was removed by centrifugation (fraction B).

(C) Enrichment of $PP_{20}$ by immunoadsorption (1) Preparation of an antiserum against $PP_{20}$ 15 g of bentonite A (Erbslöh & Co., Geisenheim/Rh.) were added to 100 ml of a solution, containing about 1 g/100 ml proteins, of fraction B in buffer solution I, and the mixture was stirred for 30 minutes and then centrifuged. This removed the major amount of the proteins contained in the solution by adsorption onto bentonite, while $PP_{20}$ remained in the supernatant. The supernatant was then concentrated to 6.5 ml using an ultrafilter, dialyzed against physiological NaCl solution, and used for the immunization of 5 rabbits. The antisera thus obtained contained antibodies against both $PP_{20}$ and some other proteins remaining in the supernatant, such as albumin, prealbumin, alpha 1-fetoprotein (AFP) and ferritin. The antiserum was made essentially specific against $PP_{20}$ by absorption with normal serum, AFP and ferritin isolated from placentae.

(2) Preparation of the immunoadsorbent 300 ml of the anti-$PP_{20}$ serum from the rabbits, obtained as described in section C 1), were dialyzed against 0.02 molar phosphate buffer (pH 7.0) and chromatographed on DEAE-cellulose to remove the immunoglobulins. The immunoglobulin fraction (1.77 g protein) was then reacted with 178 g of specially purified agarose in the form of beads (Sepharose®) supplied by Pharmacia, Uppsala, Sweden) which had been activated with 22.2 g of cyanogen bromide, and thus covalently bonded to a carrier. The procedure has been described by Axen R., Porath J., Ernbach S., Nature 214, 1302 (1967). Using an immunoadsorbent prepared in this manner, it was possible to isolate $PP_{20}$ from placental extract fractions enriched in $PP_{20}$.

(3) Procedure for immunoadsorption

The immunoadsorbent was suspended in a 0.1 molar tris HCl buffer of pH 8, which contained 1 mole/liter NaCl and 0.1 g/100 ml sodium azide (buffer solution II), packed into a chromatography column (4.5×14 cm) and washed with buffer solution II.

Then fraction B, which had been dissolved in water and dialyzed against buffer solution II, was applied to the column, whereupon $PP_{20}$ was bound by immunoadsorption. The column was thoroughly washed with buffer solution II. Then the adsorbed protein was eluted from the column with about 600 ml of 6 molar urea solution. The eluates containing $PP_{20}$ were dialyzed against buffer solution II and concentrated to about 10 ml using an ultrafilter. The yield per adsorption was about 6 mg of $PP_{20}$. The adsorbent in the column was thoroughly washed with buffer solution II immediately after the elution of $PP_{20}$. It was then possible to use it again for the binding of $PP_{20}$ by immunoadsorption.

(D) Final purification of $PP_{20}$

The protein obtained by immunoadsorption was frequently contaminated by small amounts of non-specifically bound serum proteins and other placental tissue proteins. It was possible to remove part of these accompanying proteins by gel filtration on acrylamide agarose AcA 34. The remaining impurities were then removed by reverse, or negative, immunoadsorption, that is to say using carrier-bound antibodies against the proteins still present as impurities ($PP_9$, $PP_{11}$, $PP_{16}$, AFP and serum proteins).

We claim:

1. The protein $PP_{20}$ which has the following characteristics:
   (a) an electrophoretic mobility which is somewhat faster than that of albumin,
   (b) an isoelectric point of 4.65±0.1,
   (c) a sedimentation coefficient $s_{20,w}$ of 4.1±0.1 S,
   (d) a molecular weight determined by electrophoresis in sodium dodecyl sulfate (SDS)-containing polyacrylamide gel of 50,000±10,000, the molecules of $PP_{20}$ being composed of apparently identical subunits which have a molecular weight of 27,000±3,000 and are held together non-covalently,
   (e) an extinction coefficient $E_1 \, _{cm}^{1\%}$ (280 nm) of 9.5±0.6,
   (f) a carbohydrate content of 3.0±1.3%, including mannose 0.14±0.05%, fucose 0.13±0.05%, galactose 0.61±0.2%, glucose 0.39±0.2% N-acetylglucosamine 0.95±0.3%, N-acetylgalactosamine 0.18±0.1%, N-acetylneuraminic acid 0.6±0.4%, and (g) the following aminoacid composition:

| Aminoacid | (Residues per 100 residues) mole-% | Coefficient of variation |
|---|---|---|
| Lysine | 5.36 | 0.26 |
| Histidine | 3.10 | 7.30 |
| Arginine | 3.39 | 0.63 |
| Aspartic acid | 11.45 | 1.05 |
| Threonine | 8.63 | 1.31 |
| Serine | 3.70 | 1.34 |
| Glutamic acid | 9.65 | 1.61 |
| Proline | 5.64 | 6.40 |
| Glycine | 6.96 | 1.12 |
| Alanine | 4.76 | 1.49 |
| Cystine ½ | 2.86 | 2.47 |
| Valine | 6.22 | 0.23 |
| Methionine | 1.87 | 1.51 |
| Isoleucine | 5.76 | 3.44 |
| Leucine | 11.76 | 2.65 |
| Tyrosine | 2.55 | 3.33 |
| Phenylalanine | 4.12 | 1.55 |
| Tryptophan | 2.17 | 1.30. |

2. A process for obtaining the protein $PP_{20}$ as claimed in claim 1, which comprises subjecting an extract obtained from placentae using a dilute salt or buffer solution to one or more of the following measures:

(a) precipitation of the protein $PP_{20}$ with ammonium sulfate in the pH range from 5 to 8 and at 30–70% saturation;

(b) precipitation of the protein $PP_{20}$ with a water-soluble acridine base at a pH between 4 and 7 and a concentration of the base of 0.2–0.4 g/100 ml;

(c) preparative zone electrophoresis, the protein fraction which migrates somewhat faster than albumin being isolated;

(d) gel filtration or ultrafiltration, proteins in the molecular weight range from 30,000 to 70,000 being isolated;

(e) isoelectric focusing, proteins in the pH range from 4.55 to 4.75 being isolated;

(f) adsorption of accompanying proteins onto bentonite, $PP_{20}$ remaining in solution;

(g) adsorption of the protein $PP_{20}$ onto a weakly basic ion exchanger and elution of this protein;

(h) enrichment by immunoadsorption.

3. The use of the protein $PP_{20}$ as claimed in claim 1 for obtaining an antiserum and for designing immunochemical methods for the detection and determination of this protein, in order to monitor pregnancy or to detect or check the course of diseases.

* * * * *